United States Patent
Zou et al.

(10) Patent No.: US 11,662,875 B2
(45) Date of Patent: May 30, 2023

(54) MONITOR FOR DISPLAYING PHYSIOLOGICAL AND FUNCTION INFORMATION AND DISPLAY METHOD THEREOF

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Xiaoling Zou, Shenzhen (CN); Lei Qing, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 152 days.

(21) Appl. No.: 16/859,962

(22) Filed: Apr. 27, 2020

(65) Prior Publication Data
US 2020/0257431 A1    Aug. 13, 2020

Related U.S. Application Data

(63) Continuation of application No. PCT/CN2017/107923, filed on Oct. 27, 2017.

(51) Int. Cl.
*G06F 3/04812*    (2022.01)
*A61B 5/0205*    (2006.01)
(Continued)

(52) U.S. Cl.
CPC .......... *G06F 3/04812* (2013.01); *A61B 5/021* (2013.01); *A61B 5/024* (2013.01);
(Continued)

(58) Field of Classification Search
CPC ....... A61B 5/0402; A61B 5/024; A61B 5/318; A61B 5/021; A61B 5/742; A61B 5/746;
(Continued)

(56) References Cited

U.S. PATENT DOCUMENTS

| 2011/0071420 A1 | 3/2011 | St. Pierre et al. |
| 2012/0198341 A1* | 8/2012 | Pekarske ............... G16H 40/67 715/733 |
| 2019/0298270 A1* | 10/2019 | Al-Ali .................. A61B 5/7275 |

FOREIGN PATENT DOCUMENTS

| CN | 101312686 A | 11/2008 |
| CN | 101332081 A | 12/2008 |

(Continued)

OTHER PUBLICATIONS

Extended European Search Report issued in related European Application No. 17929801.3, dated Oct. 1, 2021, 8 pages.
(Continued)

*Primary Examiner* — Yaron Cohen
(74) *Attorney, Agent, or Firm* — Bayes PLLC

(57) ABSTRACT

A display method applied to a monitor is disclosed. The method includes acquiring a first partition configuration on a display interface of a touch display screen of the monitor; displaying at least one physiological data in the first physiological data display area; displaying data other than the at least one physiological data in the first function information display area; detecting a touch screen operation received by the touch display screen; acquiring a second partition configuration of the display interface if a first touch screen operation that meets a preset re-partitioning rule is detected, the second partition configuration including a second physiological data display area, a second function information display area, and a third function information display area; partially or fully displaying at least one physiological data in the second physiological data display area; and displaying
(Continued)

data other than the at least one physiological data in the second function information display area.

24 Claims, 6 Drawing Sheets

(51) Int. Cl.
    *A61B 5/021*     (2006.01)
    *A61B 5/024*     (2006.01)
    *A61B 5/00*     (2006.01)
    *G06F 3/04886*     (2022.01)
    *A61B 5/318*     (2021.01)

(52) U.S. Cl.
    CPC .......... *A61B 5/02055* (2013.01); *A61B 5/318* (2021.01); *A61B 5/742* (2013.01); *A61B 5/746* (2013.01); *A61B 5/7475* (2013.01); *G06F 3/04886* (2013.01); *G06F 2203/04803* (2013.01)

(58) Field of Classification Search
    CPC ... A61B 5/7485; A61B 5/7445; A61B 5/7475; A61B 5/02055; G06F 3/0485; G06F 3/0486; G06F 3/04883; G06F 9/44; G06F 3/0488; G06F 3/04886; G06F 3/04812; G06F 2203/04803; G16H 40/63; G16H 10/60

See application file for complete search history.

(56) References Cited

FOREIGN PATENT DOCUMENTS

| | | |
|---|---|---|
| CN | 102129295 A | 7/2011 |
| CN | 102508663 A | 6/2012 |
| CN | 102743156 A | 10/2012 |
| CN | 103648372 A | 3/2014 |
| CN | 104305966 A | 1/2015 |
| CN | 106020664 A | 10/2016 |
| WO | 2017059597 A1 | 4/2017 |
| WO | 2017063199 A1 | 4/2017 |

OTHER PUBLICATIONS

International Search Report issued in corresponding International Application No. PCT/CN2017/107923, dated Jul. 23, 2018, 7 pages.

\* cited by examiner

MONITOR FOR DISPLAYING PHYSIOLOGICAL AND FUNCTION INFORMATION AND DISPLAY METHOD THEREOF

CROSS-REFERENCE TO RELATED APPLICATIONS

This application is a bypass continuation of PCT Application No. PCT/CN2017/107923, filed Oct. 27, 2017, which is incorporated herein by reference.

TECHNICAL FIELD

The present disclosure relates to the technical field of information interaction, and more particularly to a monitor, a display method applied to a monitor, a display device, and a storage medium.

BACKGROUND

At present, a plurality of applications are usually installed in a medical instrument. With these applications, convenient diagnosis and treatment services may be provided for patients. For example, with applications installed in a monitor, the ECG activity, respiratory cycle, body temperature, respiratory movement and cardiovascular system, etc. of a patient may be monitored in real time.

A display interface of the monitor is at least divided into a region for displaying physiological data and a region for displaying other information. When the medical personnel configure parameters of certain physiological data on the display interface, the monitor will exhibit a corresponding parameter configuration interface on the display interface.

However, the parameter configuration interface may have a situation where part or even all of the physiological data is blocked, which causes inconvenience for the medical personnel to view the physiological data in real time.

SUMMARY

The present disclosure provides a monitor, a display method applied to a monitor, a display device, and a storage medium.

In one embodiment, a monitor, comprising: at least one physiological data monitoring module, a memory, a touch display screen and a processor, wherein the at least one physiological data monitoring module is configured to monitor at least one physiological data of a patient, and the at least one physiological data comprises at least one of ECG data, blood oxygen saturation data, body temperature data, respiratory data, heart rate data, and blood pressure data;

the memory is configured to store a program and the at least one physiological data;

the touch display screen is configured to receive a touch screen operation under the control of the processor; and the processor is configured to run the program in the memory to implement the following processes:

acquiring a first partition configuration on a display interface of the touch display screen, the first partition configuration comprising a first physiological data display area and a first function information display area;

displaying the at least one physiological data in the first physiological data display area;

displaying data other than the at least one physiological data in the first function information display area;

detecting the touch screen operation received by the touch display screen;

acquiring a second partition configuration of the display interface if a first touch screen operation that meets a preset re-partitioning rule is detected, the second partition configuration comprising a second physiological data display area, a second function information display area, and a third function information display area;

displaying the at least one physiological data in the second physiological data display area;

displaying data other than the at least one physiological data in the second function information display area; and displaying at least one function button icon in the third function information display area, the function button icon being used for characterizing a corresponding function operation.

A display method applied to a monitor, the display method comprising:

acquiring a first partition configuration on a display interface of the touch display screen, the first partition configuration comprising a first physiological data display area and a first function information display area;

displaying the at least one physiological data in the first physiological data display area;

displaying data other than the at least one physiological data in the first function information display area;

detecting a touch screen operation received by the touch display screen;

acquiring a second partition configuration of the display interface if a first touch screen operation that meets a preset re-partitioning rule is detected, the second partition configuration comprising a second physiological data display area, a second function information display area, and a third function information display area;

displaying the at least one physiological data in the second physiological data display area;

displaying data other than the at least one physiological data in the second function information display area; and displaying at least one function button icon in the third function information display area, the function button icon being used for characterizing a corresponding function operation.

A display device applied to a monitor, the display device comprising: a first partition display module, a touch screen operation detection module, and a second partition display module, wherein the first partition display module is used for acquiring a first partition configuration on a display interface of the touch display screen, the first partition configuration comprising a first physiological data display area and a first function information display area; displaying the at least one physiological data in the first physiological data display area; and displaying data other than the at least one physiological data in the first function information display area;

the touch screen operation detection module is used for detecting a touch screen operation received by the touch display screen; and the second partition display module is used for acquiring a second partition configuration of the display interface if a first touch screen operation that meets a preset re-partitioning rule is detected, the second partition configuration comprising a second physiological data display area, a second function information display area, and a third function information display area; displaying the at least one physiological data in the second physiological data display area; displaying data other than the at least one physiological data in the second function information display area; and displaying at least one function button icon in the third function information display area, the function button icon being used for characterizing a corresponding function operation.

A storage medium, comprising a stored program, wherein when the program runs, a device where the storage medium is located is controlled to execute the display method applied to a monitor of any one of the above-mentioned technical solutions.

BRIEF DESCRIPTION OF THE DRAWINGS

In order to illustrate the technical solutions in the embodiments of the present disclosure or in the prior art more clearly, a brief introduction to the figures to be used in the description of the embodiments or the prior art will be provided below. Obviously, the drawings in the following description show merely the embodiments of the present disclosure, and those of ordinary skill in the art would have derived other drawings from the provided drawings without involving any inventive effort.

DETAILED DESCRIPTION OF EMBODIMENTS

Figure 1:
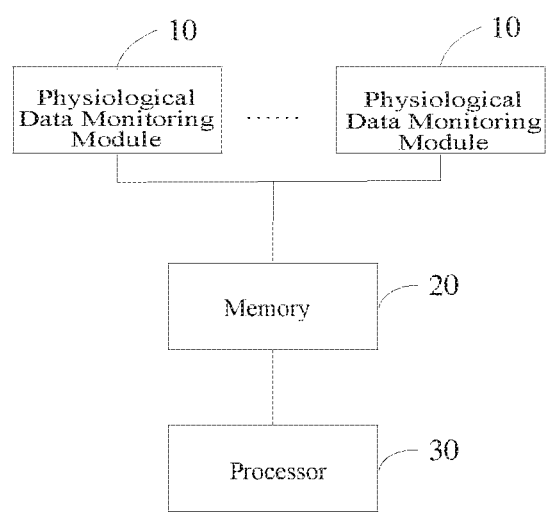
FIG. 1 shows a schematic structural diagram of a monitor.

The technical solutions of the embodiments of the present disclosure will be described below clearly and comprehensively in conjunction with the drawings of the embodiments of the present disclosure. Obviously, the embodiments described are merely some of the embodiments of the present disclosure, but not all the possible embodiments. Based on the embodiments in the present disclosure, other embodiments obtained by those of ordinary skill in the art without involving any inventive effort shall all fall within the scope of protection of the present disclosure.

The present disclosure will be further described in detail below through specific embodiments in conjunction with the accompanying drawings. Associated similar element reference numerals are used for similar elements in various embodiments. In the following embodiments, many details are described so that the present application may be better understood. However, it would be effortlessly appreciated by those skilled in the art that some of the features may be omitted or may be substituted by other elements, materials and methods in different situations. In certain cases, some operations involved in the present application are not displayed or described in the specification, which is to prevent the core part of the present application from being obscured by too much description. Moreover, for those skilled in the art, the detailed description of the involved operations is not necessary, and the involved operations may be thoroughly understood according to the description in the specification and the general technical knowledge in the art.

In addition, the characteristics, operations or features described in the specification may be combined in any appropriate manner to form various embodiments. Moreover, the steps or actions in the method description may also be exchanged or adjusted in order in a way that would have been obvious to those skilled in the art. Therefore, the various orders in the specification and drawings are merely for the purpose of clear description of a certain embodiment and are not meant to be a necessary order unless otherwise stated that a certain order must be followed.

The serial numbers themselves for the components herein, for example, "first", "second", etc., are merely used to distinguish the described objects, and do not have any sequential or technical meaning. Moreover, as used in the present application, "connection" or "coupling", unless otherwise specified, includes both direct and indirect connections (couplings).

FIG. 1 provides a structural embodiment of a monitoring and controlling instrument. The monitoring and controlling instrument comprises: at least one physiological data monitoring module 10, a memory 20, a touch display screen and a processor 30.

In this embodiment, the at least one physiological data monitoring module 10 may monitor at least one physiological data of a patient, and the physiological data may be ECG data, blood oxygen saturation data, body temperature data, respiratory data, heart rate data, and blood pressure data, etc. For example, in some embodiments, the monitor comprises two physiological data monitoring modules for monitoring ECG data and blood oxygen saturation data of a patient. Moreover, the physiological data monitoring module 10 mentioned in this embodiment may acquire the collected original physiological data from an external physiological sensor, and then process the original physiological data to obtain physiological data that may be displayed on a display device. Different physiological data monitoring modules 10 may be used for different physiological data.

Of course, in some embodiments, the at least one physiological data monitoring module 10 may be integrated on one or more motherboards, or may be integrated on one or more processes. Moreover, in some embodiments, the at least one physiological data monitoring model 10 may be built in a monitor housing or externally placed outside the monitor housing. For example, the at least one physiological data monitoring module 10 may be connected to the monitor in an externally pluggable manner.

In this embodiment, the memory 20 is used for storing a program and the at least one physiological data. The program in this embodiment may include a processing program for processing the above-mentioned original physiological data or a program for processing the above-mentioned original physiological data and then displaying same on the touch display screen or other display device.

Of course, in some embodiments, the memory 20 may be integrated with the processor 30 or may be a separately provided storage device, for example, it may be a cache or a hard disk light storage device. Moreover, the memory 20 may also be used for storing programs related to processes such as detection, processing, tracking, and feedback of touch screen operations.

Specifically, in this embodiment, a touch display screen is used as a display device. The touch display screen is used for displaying one or more of the above-mentioned physiological data, and may also receive the touch screen operation input by a user. The touch screen operation here may be a sliding operation input on the touch display screen, for example, one or more of gesture operations performed according to a predetermined rule such as a single-finger sliding operation, a multi-finger sliding operation, and a tapping operation. Moreover, the touch display screen may also be used for receiving the touch screen operation under the control of the processor.

In this embodiment, a connection is established between the at least one physiological data monitoring module 10 and the memory 20, and between the memory 20 and the processor 30 via a bus system, which enables the memory to communicate with each physiological data monitoring module 10 and the processor 30, respectively.

Figure 2:
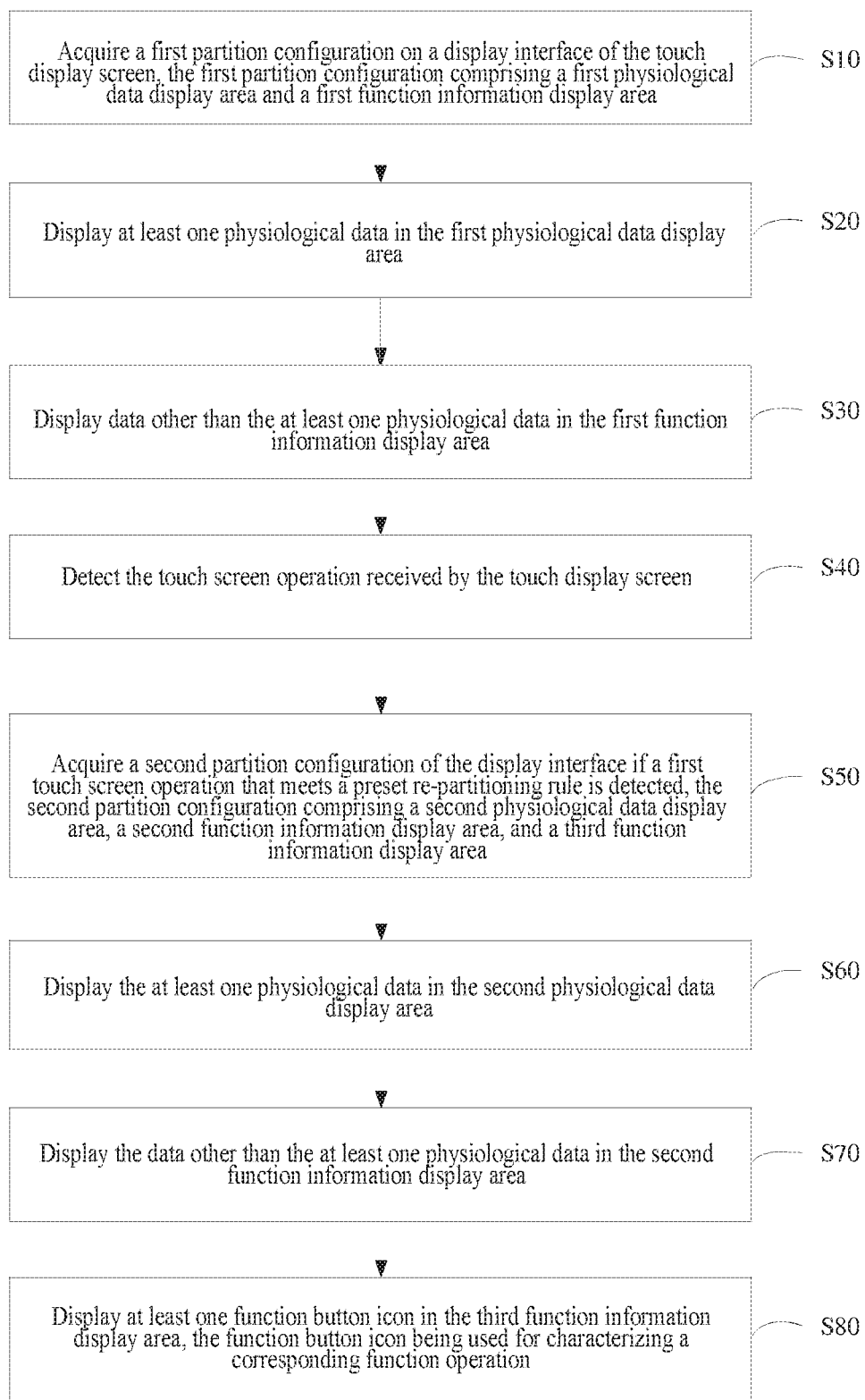
FIG. 2 shows a method flowchart of a display method applied to a monitor.

FIG. 2 provides a method for displaying physiological data implemented on the monitor, which may be specifically described in combination with the structural embodiment of the monitoring and controlling instrument shown in FIG. 1. The processor 30 is used for running the program in the memory 20 to implement the following processes:

In step S10, a first partition configuration on a display interface of the touch display screen is acquired, the first partition configuration comprising a first physiological data display area and a first function information display area.

In one of the embodiments of this step, for each physiological indicator of the patient, there is a corresponding physiological data monitoring module for monitoring. For example, for one or more physiological indicators of the ECG activity, respiratory cycle, body temperature, and respiratory movement of the patient, the monitor has a corresponding physiological monitoring module to monitor one or more physiological data of the corresponding ECG data, blood oxygen saturation data, body temperature data, and respiratory data.

Each physiological data monitoring module 10 monitors each physiological indicator of the patient in real time, and sends the monitored physiological data to the memory 20 in real time, so that the memory 20 may store the physiological data. Of course, the patient-related physiological data obtained by monitoring in real time by each physiological data monitoring module may also be displayed on the display device, for example, on the touch display screen.

However, the display device often may not display the required information on one display interface at the same time due to the limitation of the size of the display screen, so the display interface needs to be arranged as needed. The processor 30 may perform the partition configuration of the display interface according to the use occasion or mode setting of the monitor. The partition configuration of the monitor comprises at least a physiological data display area and a function information display area therein. The physiological data display area may be used for displaying the physiological data monitored by the physiological data monitoring module 10 therein. The function information display area may be used for displaying function information of the monitor therein. The function information comprises one or more of function configurations, function attributes, and function buttons. For example, the content displayed in the function information display area comprises, but is not limited to, one or more of patient information, alarm information, power information, volume information, attribute configuration buttons, and wireless information, which is not specifically limited in this embodiment.

Usually, the monitor needs to monitor the physiological indicators of the patient in real time. The first physiological data display area and the first function information display area in the first partition configuration may be the physiological data display area and the function information display area at the first moment for displaying the physiological data and the function information of the monitor obtained at the first moment. Alternatively, in some embodiments, the first physiological data display area and the first function information display area in the first partition configuration may be the partition configuration of the display interface in a first state of the monitor, and the first state may be specifically a monitoring mode. For example, the monitoring mode may be a first monitoring mode for a critically ill patient or a second monitoring mode for a sub-critically ill patient, etc.

However, in order to facilitate viewing the physiological data by medical personnel, in some embodiments, the areas of the first physiological data display area and the first function information display area may be preset, so that the area of the first physiological data display area occupies most of the entire display interface, and the area of the first physiological data display area is greater than that of the first function information display area. Also, in order to facilitate modifying the function attributes by the medical personnel, for example, modifying the information of the patient being monitored, adjusting the volume information, or changing the wireless information, etc., the first function information display area may be located at the edge of the display interface of the monitor. In one of the embodiments, the first physiological data display area displays textual/numerical information (such as 1001 in FIG. 3) and waveform data (such as 1002 in FIG. 3) of at least one physiological parameter.

In step S20, at least one physiological data is displayed in the first physiological data display area.

In one of the embodiments of this step, the at least one physiological data may be obtained by the at least one physiological data monitoring module 10 of the monitor in FIG. 1, or the at least one physiological data may be physiological data obtained after the processor processes the original physiological data obtained by the at least one physiological data monitoring module 10.

In step S30, data other than the at least one physiological data is displayed in the first function information display area.

In one of the embodiments of this step, the first function information display area is used for displaying one or more of function configurations, function attributes, and function buttons of the monitor. Therefore, the data other than the at least one physiological data comprises, but is not limited to, one or more of patient information, alarm information, power information, volume information, wireless information, and attribute configuration buttons, which is not specifically limited in this embodiment. For example, the first function information display area may display a function configuration window, through which the layout of the display interface, font size, display content of the display area, etc. may be adjusted. As another example, the first function information display area may also display the function attributes, and the function attributes comprise at least one or more of patient information, alarm information, power information, volume information, and wireless information, etc. As yet another example, the first function information display area may also display the function buttons, for example, at least one or more of a configuration button, a menu button, etc. Specifically, the function buttons here are the result of a deep-level multi-level menu, and multiple steps are needed to complete the search for a certain function.

The processor may adjust the partition layout on the display interface by calling the program in the memory, and generate corresponding soft buttons or text and graphic information to represent the above-mentioned function configurations, function attributes, or function buttons.

Figure 3:
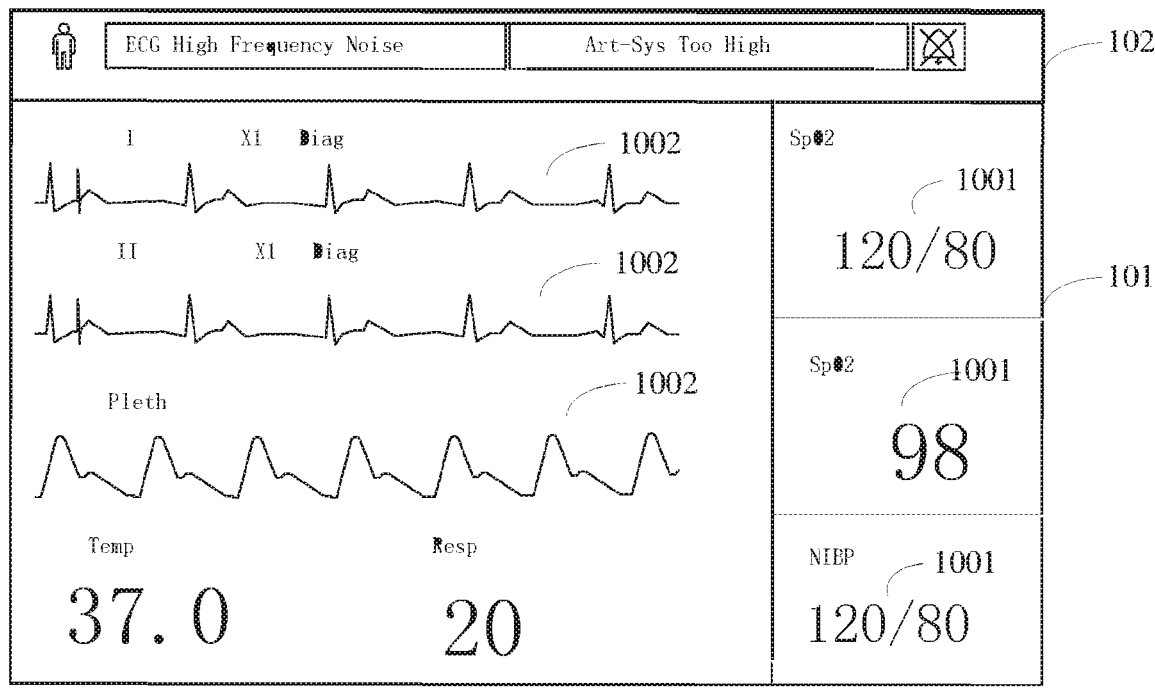
FIG. 3 shows a monitor display interface in a normal display mode.

FIG. 3 provides a monitor display interface in a normal display mode. The display interface here comprises two display areas. One is the first physiological data display area 101, the physiological data is displayed in the first physiological data display area 101, and the physiological data is further divided into the textual/numerical information 1001 and the waveform data 1002; and the other one is the first function information display area 102, the function information is displayed in the first function information display area 102, and the function information is the function button, alarm information, and volume information successively. Tapping the function button 1021 may pop up the function configuration window related to the monitoring attribute configuration and interface icon configuration, etc. For example, tapping the function button may pop up a configuration interface related to monitoring items, monitoring information, monitoring attributes, and function icon configuration, etc. Of course, for the first physiological data display area 101, different display positions may also be configured for different physiological indicators, which is not specifically limited in this embodiment.

In step S40, the touch screen operation received by the touch display screen is detected.

In one of the embodiments of this step, the processor detects the touch screen operation received by the touch display screen by calling the program in the memory.

The touch display screen may determine touch points on the screen by detecting capacitance transformation, and the touch points based on the touch display screen are processed to form a touch trajectory, thereby determining a touch screen operation corresponding to the touch trajectory. In some embodiments, the touch screen operation comprises one or more of the gesture operations performed according to the predetermined rule such as the single-finger sliding operation, the multi-finger sliding operation, and the tapping operation.

In step S50, a second partition configuration of the display interface is acquired if a first touch screen operation that meets a preset re-partitioning rule is detected, the second partition configuration comprising a second physiological data display area, a second function information display area, and a third function information display area.

In one of the embodiments of this step, in order to avoid that the display device may not display the information required by medical personnel on one display interface at the same time, the display interface may be arranged as needed, that is, the re-partitioning rule may be preset according to the use occasion or mode setting of the monitor. The re-partitioning rule comprises the display position, display content, and other display parameters of the physiological data display area and function information display area after partitioning. For example, in order to facilitate viewing the physiological data by the medical personnel, the partitioned physiological data display area is arranged at the middle position. However, the re-partitioning rule is preset with a corresponding trigger operation and the triggered partition configuration. The trigger operation here may be the touch screen operation, such as one of the single-finger sliding operation, the multi-finger sliding operation, and the tapping operation.

The physiological data display area in the second partition configuration may be used for displaying the physiological data monitored by the physiological data monitoring module 10 therein. The partitioned function information display area may not only be used to display the function information of the monitor, but also to display the function button icons therein. The function button icon here is a button icon predefined by the user as a hot key or other shortcut operation interface and is the result of a single-level menu, and only one step is needed to complete the search for a certain function. The function information is consistent with the function information disclosed in step S10 described above, including, but not limited to, one or more of patient information, alarm information, power information, volume information, attribute configuration buttons, and wireless information, which is not specifically limited in this embodiment.

Usually, the monitor needs to monitor the physiological indicators of the patient in real time. The second physiological data display area and the second function information display area in the second partition configuration may be the physiological data display area and the function information display area at the second moment for displaying the physiological data and the function information of the monitor obtained at the second moment. Alternatively, in some embodiments, the second physiological data display area and the second function information display area in the second partition configuration may be the partition configuration of the display interface in a second state of the monitor, and the second state may be specifically a monitoring mode. For example, the monitoring mode may be a first monitoring mode for a critically ill patient or a second monitoring mode for a sub-critically ill patient, etc. Moreover, for the second partition configuration at the second moment or in the second state, since the display content of the first physiological data display area may be displayed in the second physiological data display area, the second partition configuration will not affect the continuity and effectiveness of the monitoring of the physiological indicators.

During switching the partition configurations, the data in different physiological data display areas are continuously displayed, so that it is ensured that the monitor monitors in real time and continuously displays the physiological data.

In step S60, the at least one physiological data is displayed in the second physiological data display area.

In one of the embodiments of this step, the at least one physiological data may be obtained by the at least one physiological data monitoring module 10 of the monitor in FIG. 1, or the at least one physiological data may be physiological data obtained after the processor processes the original physiological data obtained by the at least one physiological data monitoring module 10. The textual/numerical information 1001 and the waveform data 1002 may be displayed in the second physiological data display area, or only the textual/numerical information 1001 is displayed in the second physiological data display area.

In step S70, data other than the at least one physiological data is displayed in the second function information display area.

In one of the embodiments of this step, the second function information display area is used for displaying the function attributes of the monitor. Therefore, the data other than the at least one physiological data comprises, but is not limited to, one or more of patient information, alarm information, power information, volume information, wireless information, and attribute configuration buttons, which is not specifically limited in this embodiment. For example, the second function information display area may display the function configuration window, through which the layout of the display interface, font size, display content of the display area, etc. may be adjusted. As another example, the second function information display area may also display the function attributes, and the function attributes comprise at least one or more of patient information, alarm information, power information, volume information, and wireless information, etc. As yet another example, the second function information display area may also display the function buttons, for example, at least one or more of the configuration button, the menu button, etc. Specifically, the function buttons here are the result of the deep-level multi-level menu, and multiple steps are needed to complete the search for a certain function.

In step S80, at least one function button icon is displayed in the third function information display area, the function button icon being used for characterizing a corresponding function operation.

The function button icon here is a button icon predefined by the user as a hot key or other shortcut operation interface, the corresponding button is the result of the single-level menu, and only one step is needed to complete the search for a certain function.

Specifically, the at least one function button icon comprises at least one soft button associated with the function operation. The function operation comprises: attribute configuration, interface configuration, alarm off, alarm on, measurement startup, shutdown, standby, etc. Each function button icon corresponds to one function operation, and the user taps the corresponding function button icon to enter the corresponding function operation interface or window, or the processor obtains the corresponding function instruction directly based on the user's tapping operation to perform the corresponding operation. For example, when the user taps the function button icon characterizing the alarm off, the monitor turns off the current alarm. When the user taps the function button icon characterizing the attribute configuration, the processor pops up an attribute configuration window or the function configuration window on the display interface.

Based on this, the first touch screen operation that meets the preset re-partitioning rule may comprise a parameter configuration operation, based on which, the above-mentioned window is popped up, for example, the above-mentioned attribute configuration window or the function configuration window is popped up. Of course, the above-mentioned first touch screen operation may also be a touch screen operation for triggering the second partition configuration, such as an operation of a hot-key display operation. Specifically, the first touch screen operation may be preset by medical personnel.

In one of the embodiments, the processor 30 detects the touch screen operation received by the touch display screen in real time; and the second partition configuration is further acquired if the first touch screen operation that meets the preset re-partitioning rule is detected. The second partition configuration comprises the second physiological data display area, the second function information display area, and the third function information display area. A display interface after re-partitioning is shown as in FIG. 4a. In this display interface, the second physiological data display area 202 is arranged between the second function display area 201 and the third function display area 203. Compared with the display interface shown in FIG. 3, the area of the second physiological data display area 201 is smaller than that of the first physiological data display area 101, and the area of the second function information display area 201 is greater than or equal to that of the first function information display area 102.

Still further, in one of the embodiments, the content displayed in the second function display area 201 comprises the content displayed in the first function display area. Alternatively, the second function display area 201 comprises a window popped up on the display interface therein, and this window comprises the above-mentioned attribute configuration window or the function configuration window, for example, the second function display area 201 in FIG. 4a comprises a pop-up window.

Figure 4A:
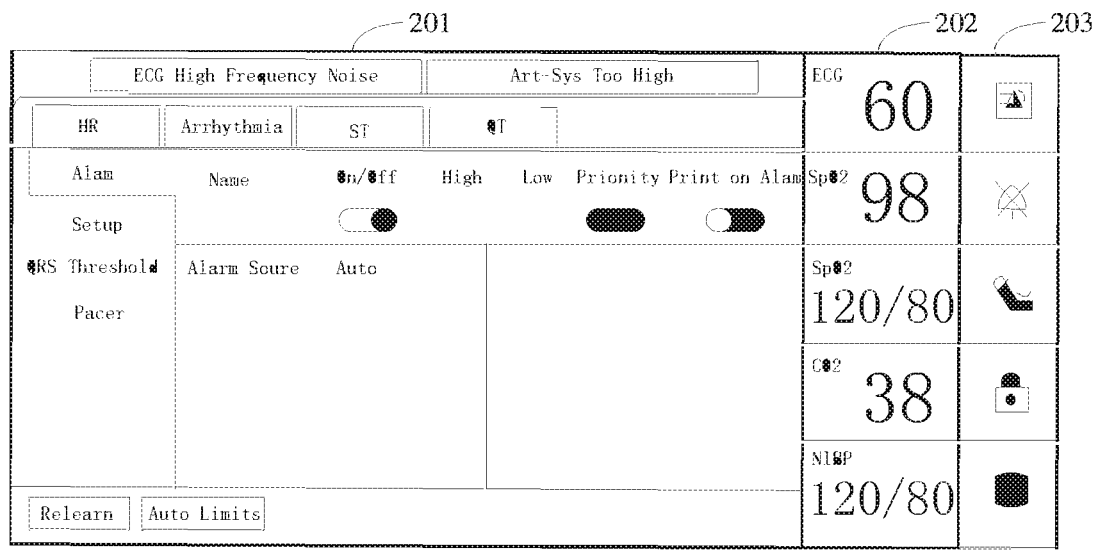
FIG. 4a shows a display interface after re-partitioning.

In the embodiment of FIG. 4a, the display of the second function display area 201 may not cover the display area of the physiological data by re-partitioning the display interface. Moreover, in one of the embodiments, the second physiological data display area displays the textual/numerical information related to the physiological data. Generally, the display related to the physiological data comprises the textual/numerical information (such as 1001 in FIG. 3) and the waveform data (such as 1002 in FIG. 3). In one of the embodiments, the physiological parameters displayed in the second physiological data display area do not comprise the waveform data. The textual/numerical information comprises numerical information of basic parameters, for example, at least one of the ECG data, blood oxygen saturation data, body temperature data, respiratory data, heart rate data, and blood pressure data, etc. In one of the embodiments, the second physiological data display area displays the textual/numerical information of the at least one physiological parameter, but does not display the waveform data. The second physiological data display area, the second function information display area, and the third function information display area are arranged side by side on the display interface.

Figure 4B:
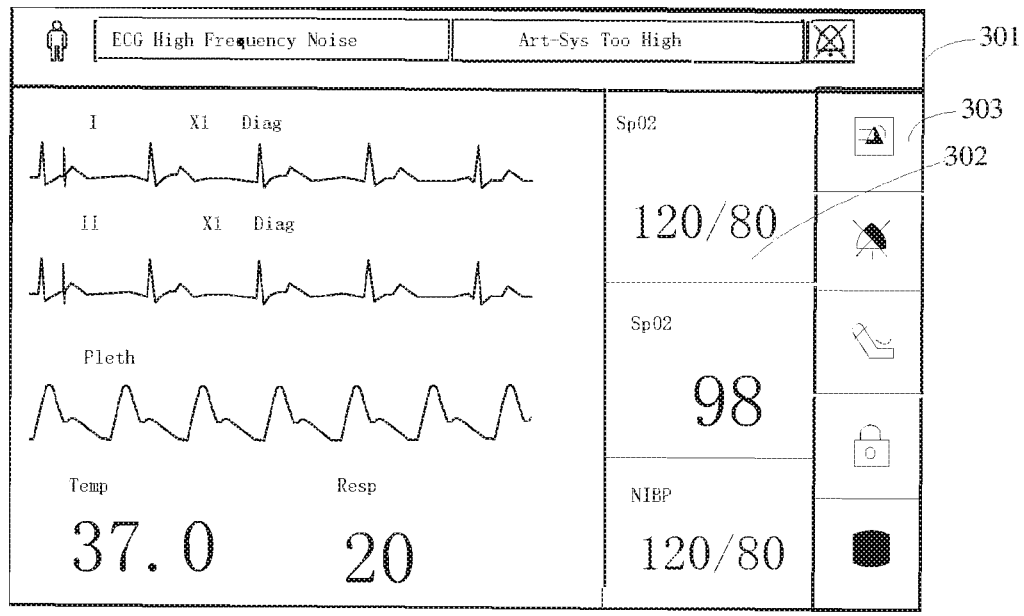
FIG. 4b shows another display interface after re-partitioning.

In one of the embodiments, after the first touch screen operation, the second partition configuration is acquired, so that the processor forms an interface distribution as shown in FIG. 4b on the display interface. The second partition configuration comprises a second physiological data display area 302, a second function information display area 301 and a third function information display area 303. The second physiological data display area 302 displays textual/numerical information (such as 1001 in FIG. 3) and waveform data (such as 1002 in FIG. 3) of at least one physiological parameter. The content displayed in the second function information display area 301 comprises, but is not limited to, one or more of patient information, alarm information, power information, volume information, attribute configuration buttons, and wireless information, which is not specifically limited in this embodiment. A hidden display area for displaying the function button icons is displayed without covering the normal displayed physiological parameter display area, thereby ensuring that the user will not affect the real-time observation of the physiological parameters due to operations such as the adjustment of configurations or the appearance of alarm information during use.

In one of the embodiments, in order to facilitate quickly finding some function button icons by the medical personnel, the third function information display area (such as 203 in FIGS. 4a and 303 in FIG. 4b) may be located at the edge of the display interface. Still further, the third function display area and the first function information display area are vertically arranged on the display interface of the touch display screen and are respectively located at edge positions, specifically referring to 203, 201 and 303, 301 in FIG. 4a and FIG. 4b. Therefore, by re-partitioning, there is no case where the function display area covers the physiological parameter display area.

Still further, in one of the embodiments, the above-mentioned method further comprises the following steps:

after the first partition configuration of the display interface is acquired, acquiring the second partition configuration of the display interface if an alarm event is detected, the second partition configuration comprising a second physiological data display area, a second function information display area, and a third function information display area; displaying the at least one physiological data in the second physiological data display area; displaying data other than the at least one physiological data in the second function information display area; and displaying at least one function button icon in the third function information display area, the function button icon being used for characterizing a corresponding function operation.

In this embodiment, the alarm event comprises, but is not limited to, a physiological alarm and a technical alarm. Specifically, the physiological alarm refers to an alarm issued when the physiological data monitoring module detects that the physiological data exceeds an alarm threshold, for example, an alarm issued when an ECG data monitoring module detects that the patient's heart rate exceeds 140 times/minute; and the technical alarm is an alarm event caused by a failure of some device in the monitor, for example, the ECG data monitoring module is short-circuited, and as another example, the memory has an insufficient storage space, etc.

In one embodiment, the above-mentioned steps are implemented by the processor running the program in the memory. Based on this embodiment, the re-acquisition of the partition configuration may be automatically triggered when the monitor automatically detects the alarm event, thereby changing the partition configuration of the touch display screen to the second partition configuration.

For example, in one of the embodiments, after acquiring the first partition configuration of the display interface, the monitor displays the display interface as shown in FIG. 3, and when the processor detects the alarm event, the second partition configuration is automatically acquired and the display interface is adjusted to be under the display layout shown in FIG. 4b. In the specific implementation process, the second physiological data display area displays the textual/numerical information and the waveform data of the at least one physiological parameter, and the content displayed in the second function information display area comprises, but is not limited to, one or more of patient information, alarm information, power information, volume information, attribute configuration buttons, and wireless information, which is not specifically limited in this embodiment. The related explanation of the function information display area mentioned in the foregoing may be referred to for details. In one of the embodiments, the second function information display area does not display the pop-up window, for example, the above-mentioned attribute configuration window or the function configuration window.

In some of the embodiments, the above-mentioned method further comprises the following step:

switching the display interface from the second partition configuration to the first partition configuration if the duration of the alarm event exceeding a first preset duration is detected and no other touch screen operation is detected within the first preset duration. In one embodiment, the above-mentioned step is implemented by the processor running the program in the memory. Based on the monitoring of time, the layout of the display interface may be automatically adjusted.

In some of the embodiments, the above-mentioned method further comprises the following step:

switching the display interface from the second partition configuration to the first partition configuration when any one of the following conditions is satisfied;

no other touch screen operation is detected within the first preset duration; a second touch screen operation is detected in a preset region of the display interface; and a third touch screen operation that meets a first preset operation trajectory is detected.

In one embodiment, the above-mentioned step is implemented by the processor running the program in the memory. The second touch screen operation or the third touch screen operation may comprise at least one of gesture operations performed according to the predetermined rule such as the sliding operation, the single-finger sliding operation, the multi-finger sliding operation, and the tapping operation input on the touch display screen. The preset operation trajectory comprises a movement trajectory of the touch screen operation on the display interface at a position where an input portion (for example a user's finger) is in contact with a touch screen. The preset operation trajectory comprises, but is not limited to, a point contact, a linear movement trajectory, and a curved movement trajectory, etc. Of course, the first preset operation trajectory may be compared with the movement trajectory corresponding to the third touch screen operation input in the second physiological parameter display area or the second function information display area or in the entire display interface. The preset region may comprise any one of positions in the second physiological parameter display area or the second function information display area. Based on the monitoring of the touch screen operation, the layout of the display interface may be automatically adjusted.

In some of the embodiments, the above-mentioned method for displaying the physiological parameter further comprises the following steps:

displaying a first part of the at least one function button icon in the third function information display area; and if a fourth touch screen operation that meets a second preset operation trajectory is detected in the third function information display area, in response to the fourth touch screen operation, displaying a second part of the at least one function button icon in the third function information display area.

Figure 4C:
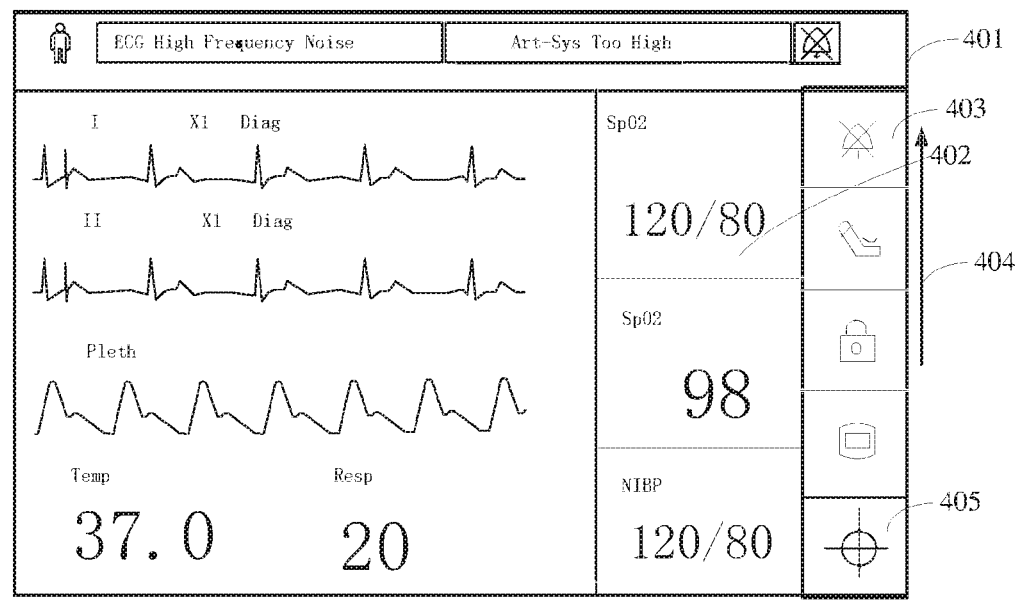
FIG. 4c shows another display interface after re-partitioning.

In one embodiment, the above-mentioned steps are implemented by the processor running the program in the memory. The second preset operation trajectory in this embodiment comprises, but is not limited to, the point contact, the linear movement trajectory, and the curved movement trajectory, etc. The fourth touch screen operation may be a linear movement corresponding to the touch screen operation in the third function information display area at a position where the input portion is in contact with the touch screen, for example, a linear movement of the contact position of the input portion with the touch screen in the third function information display area 403 in a direction 404 indicated by an arrow in FIG. 4c. The second function information display area 401 is the second function information display area as mentioned above, and the second physiological parameter display area 402 is the second physiological parameter display area as mentioned above. The first part of the at least one function button icon is a combination of the function button icons as shown in a region 303 in FIG. 4b, the second part of the at least one function button icon is a combination of the function button icons as shown in a region 403 in FIG. 4c, and there are different function button icons between the two combinations, such as a function button icon 405.

In some of the embodiments, the above-mentioned method further comprises the following steps:

displaying a first part of the at least one function button icon in the third function information display area; and if a fifth touch screen operation for characterizing the movement of a target function button icon is detected in the third function display area, in response to the fifth touch screen operation, moving the target function button icon to a target position, and rearranging all the function button icons in the third function information area.

Figure 4D:
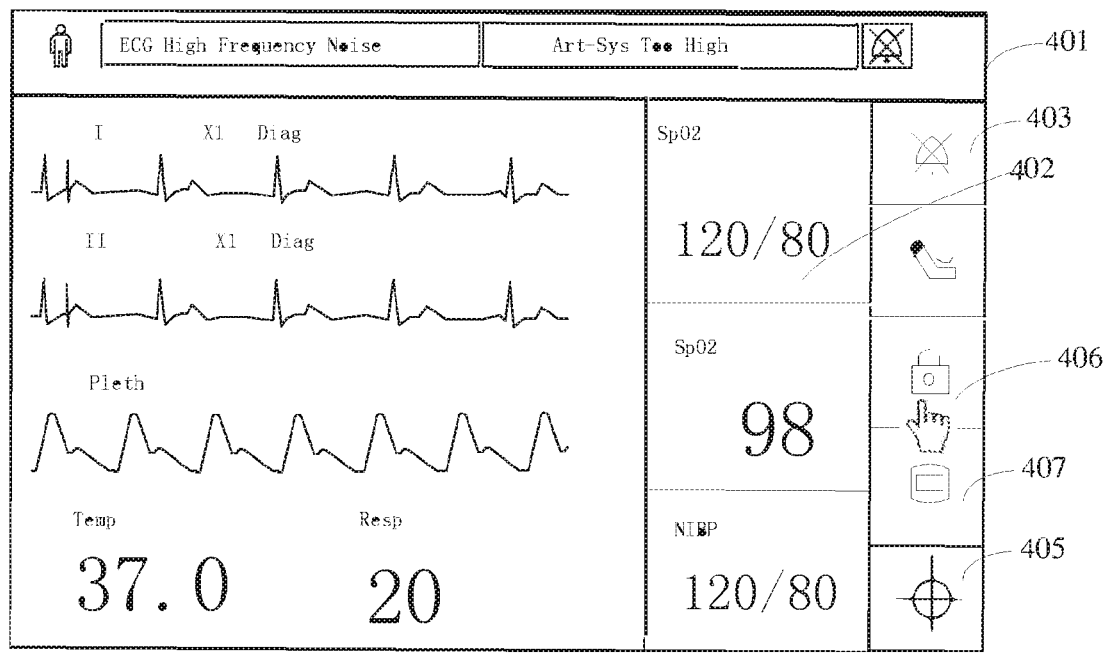
FIG. 4d shows another display interface after re-partitioning.
Figure 4E:
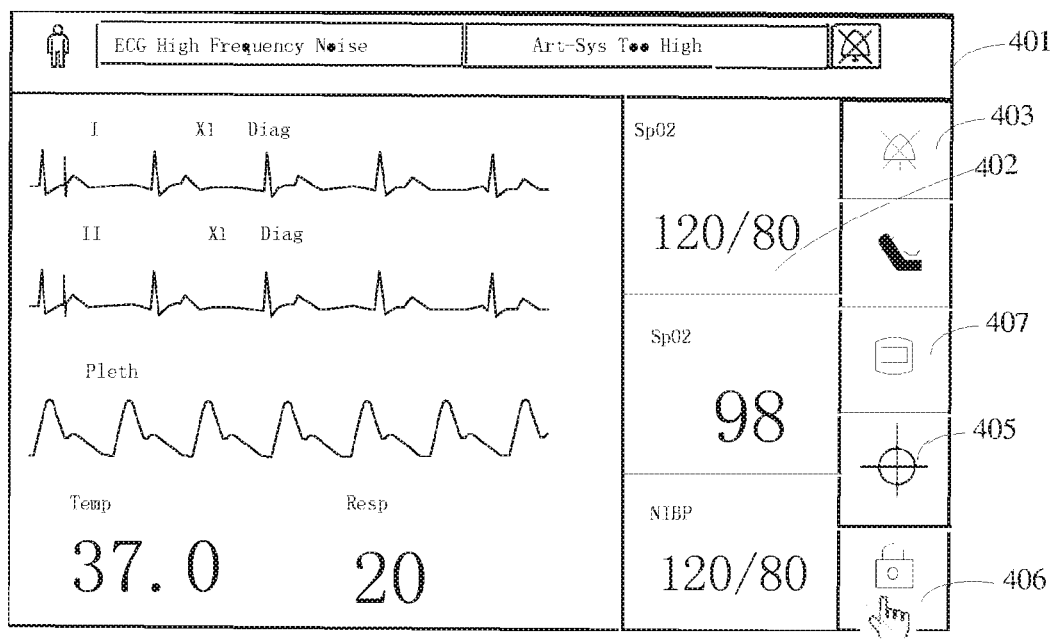
FIG. 4e shows another display interface after re-partitioning.

In one of the embodiments, as shown in FIG. 4d, if a finger continuous tapping or sliding operation 406 is detected in the region of a lock screen button icon located in the third function information display area 403, the operation is further tracked and responded to. It is assumed that when the lock screen button icon is located at the function button icon 405, the finger continuous tapping or sliding operation 406 disappears, the lock screen button icon is arranged to the function button icon 405, correspondingly, a function button icon 407 is moved to the original position of the lock screen button icon, and the function button icon 405 is moved to the original position of the function button icon 407. At this time, the display interface is as shown in FIG. 4e. The above-mentioned target position is positioned by tracking the movement trajectory operated by touching the display screen on the display interface at a position where the input portion (for example the user's finger) is in contact with the touch display screen. For example, the obtained movement trajectory is tracked to determine the target position corresponding to the fifth touch screen operation, thereby rearranging the function button icons.

In one embodiment, the above-mentioned steps are implemented by the processor running the program in the memory.

In some of the embodiments, the above-mentioned method further comprises the following steps:

after the second partition configuration of the display interface is acquired, acquiring a third partition configuration of the display interface if a sixth touch screen operation for characterizing the hiding of function buttons is detected, the third partition configuration comprising a third physiological data display area and a fourth function information display area; displaying the content displayed in the first physiological data display area in the third physiological data display area; and displaying the content displayed in the first function information display area in the fourth function information display area.

Figure 4F:
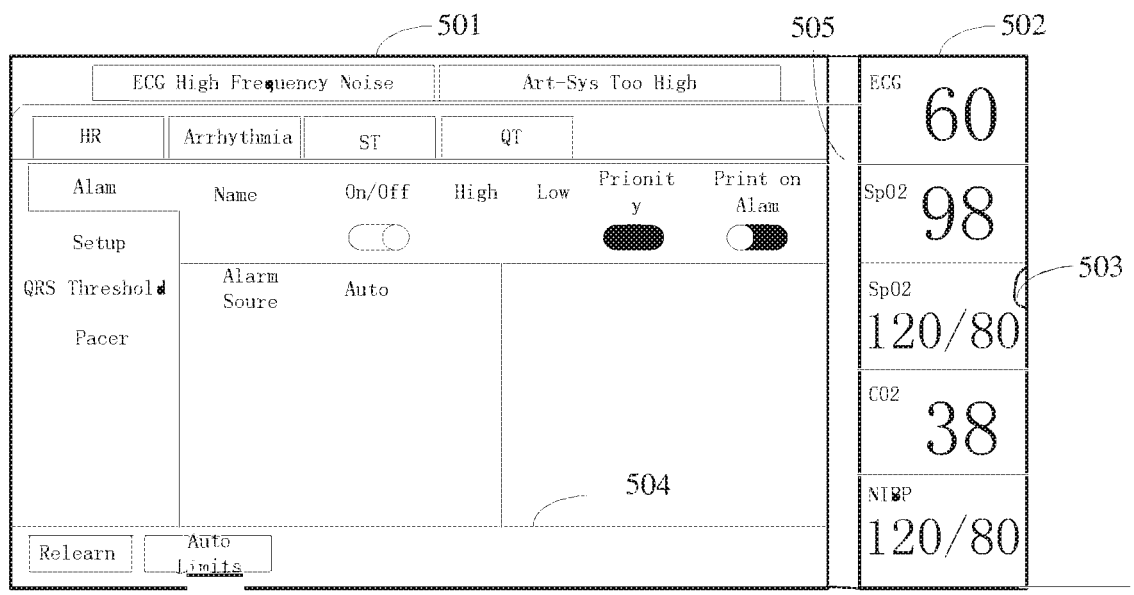
FIG. 4f shows another display interface after re-partitioning.

Still further, in one of the embodiments, based on the display interface obtained in the above-mentioned second partition configuration, the second function information display area comprises the foregoing pop-up window, and the third function information display area displays the textual/numerical information of the at least one physiological parameter instead, but does not display the waveform data. For example, as shown in FIG. 4f, when a window 504 is popped up in a second function information display area 501, the window is suspended over part or all of a second physiological data display area 505, and the textual/numerical information of the at least one physiological parameter in the second physiological data display area 505 is extracted to be displayed in the third function information display area 502. At this time, the function button icons originally displayed in the third function information display area are collectively transparent or hidden. The triggering of the function button icons originally displayed in the third function information display area to be collectively transparent or hidden may be based on the sixth touch screen operation, for example, tapping a soft button 503 (FIG. 4f). For example, by tapping the soft button 503, the function button icons originally displayed in the third function information display area may be expanded and displayed, so as to switch between the display of the function button icons and the display of the textual/numerical information of the physiological parameters in the third function information display area. Of course, it is also possible that by tapping the soft button 503, the function button icons originally displayed in the third function information display area are expanded and are formed in the third function information display area, and also the function button icons and the textual/numerical information of the physiological parameters are displayed, which is similar to the FIG. 4a.

In one embodiment, the above-mentioned steps are implemented by the processor running the program in the memory. Based on this embodiment, it is possible to hide the function buttons when the medical personnel does not need the function buttons to avoid occupying the display interface thereby. Of course, in one of the embodiments, when the processor detects a corresponding touch screen operation, for example, a touch screen operation for characterizing the hiding of the function buttons, the second partition configuration of the display interface is restored to the first partition configuration.

Moreover, in order to facilitate viewing monitoring data in real time by more medical personnel, an external expansion screen may be connected to the monitor. The external expansion screen is connected to the processor and may simultaneously display the content displayed in the display interface, of course, or simultaneously display for a certain display region, or display for function keys such as hidden function hot keys, which is not specifically limited in this embodiment and may be specifically configured according to actual needs.

The monitor provided by the embodiments of the present disclosure may switch the display interface from the first partition device to the second partition configuration when the first touch screen operation that meets the preset re-partitioning rule is detected. Since parameter configuration related data, physiological data and function button icons may be separately displayed in the second partition configuration, the problem that a parameter configuration interface blocks part or even all of the physiological data may be solved, thereby facilitating viewing monitoring data in real time by the medical personnel.

Figure 5:
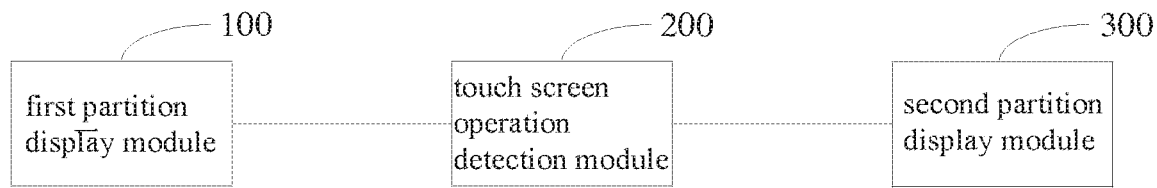
FIG. 5 shows a schematic structural diagram of a display device of a monitor.

Based on the description of the monitor structure and the display method applied to the monitor in the above-mentioned embodiments, FIG. 5 provides a structural embodiment of a display device of a monitor, the display device comprising: a first partition display module 100, a touch screen operation detection module 200, and a second partition display module 300, wherein the first partition display module 100 is used for acquiring a first partition configuration on a display interface of a touch display screen, the first partition configuration comprising a first physiological data display area and a first function information display area; displaying at least one physiological data in the first physiological data display area; and displaying data other than the at least one physiological data in the first function information display area;

the touch screen operation detection module 200 is used for detecting a touch screen operation received by the touch display screen; and the second partition display module 300 is used for acquiring a second partition configuration of the display interface if a first touch screen operation that meets a preset re-partitioning rule is detected, the second partition configuration comprising a second physiological data display area, a second function information display area, and a third function information display area; displaying the at least one physiological data in the second physiological data display area; displaying data other than the at least one physiological data in the second function information display area; and displaying at least one function button icon in the third function information display area, the function button icon being used for characterizing a corresponding function operation.

In this embodiment, the specific execution process of the first partition display module 100 is consistent with that of steps S10 to S30 in the above-mentioned embodiments, the specific execution process of the touch screen operation detection module 200 is consistent with that of step S40 in the above-mentioned embodiments, and the specific execution process of the second partition display module 300 is consistent with that of steps S50 to S80 in the above-mentioned embodiments, which is not described in this embodiment, please refer to the disclosure of the above-mentioned embodiments.

In some of the embodiments, the above-mentioned device further comprises the following module:

a third partition display module for, after the first partition configuration of the display interface is acquired, acquiring the second partition configuration of the display interface if an alarm event is detected, the second partition configuration comprising a second physiological data display area, a second function information display area, and a third function information display area; displaying the at least one physiological data in the second physiological data display area; displaying data other than the at least one physiological data in the second function information display area; and displaying at least one function button icon in the third function information display area, the function button icon being used for characterizing a corresponding function operation.

In some of the embodiments, the above-mentioned device further comprises the following module:

a first partition switching module for switching the display interface from the second partition configuration to the first partition configuration if the duration of the alarm event exceeding a first preset duration is detected and no other touch screen operation is detected within the first preset duration.

In some of the embodiments, the above-mentioned device further comprises the following module:

a second partition switching module for switching the display interface from the second partition configuration to the first partition configuration when any one of the following conditions is satisfied;

no other touch screen operation is detected within the first preset duration; a second touch screen operation is detected in a preset region of the display interface; and a third touch screen operation that meets a first preset operation trajectory is detected.

In some of the embodiments, the above-mentioned device further comprises the following module:

a fourth partition display module for displaying a first part of the at least one function button icon in the third function information display area; and if a fourth touch screen operation that meets a second preset operation trajectory is detected in the third function information display area, in response to the fourth touch screen operation, displaying a second part of the at least one function button icon in the third function information display area.

In some of the embodiments, the above-mentioned device further comprises the following module:

a fifth partition display module for displaying a first part of the at least one function button icon in the third function information display area; and if a fifth touch screen operation for characterizing the movement of a target function button icon is detected in the third function display area, in response to the fifth touch screen operation, moving the target function button icon to a target position, and rearranging all the function button icons in the third function information area.

In some of the embodiments, the above-mentioned device further comprises the following module:

a sixth partition display module for, after the second partition configuration of the display interface is acquired, acquiring a third partition configuration of the display interface if a sixth touch screen operation for characterizing the hiding of function buttons is detected, the third partition configuration comprising a third physiological data display area and a fourth function information display area; displaying the content displayed in the second physiological data display area in the third physiological data display area; and displaying the content displayed in the second function information display area in the fourth function information display area.

The display device applied to a monitor provided by the embodiments of the present disclosure may switch the display interface from the first partition device to the second partition configuration when the first touch screen operation that meets the preset re-partitioning rule is detected. Since parameter configuration related data, physiological data and function button icons may be separately displayed in the second partition configuration, the problem that a parameter configuration interface blocks part or even all of the physiological data may be solved, thereby facilitating viewing monitoring data in real time by the medical personnel.

Embodiments of the present disclosure provide a storage medium on which a program is stored, and when the program is executed by a processor, the display method applied to a monitor is implemented.

Those skilled in the art would have understood that all or some of the functions of the various methods in the above embodiments may be implemented by means of hardware or by means of a computer program. When all or some of the functions in the above embodiments are implemented by means of a computer program, the program may be stored in a computer-readable storage medium, and the storage medium may include: a read-only memory, a random access memory, a magnetic disk, an optical disk, a hard disk, etc., and the program is executed by a computer to achieve the above functions. For example, the program is stored in a memory of the device, and when the program in the memory is executed by the processor, all or some of the above functions may be implemented. In addition, when all or some of the functions in the above embodiments are implemented by means of a computer program, the program may also be stored in a storage medium such as a server, another computer, a magnetic disk, an optical disk, a flash disk or a mobile hard disk, may be saved to a memory of a local device by downloading or copying, or may perform version updating on the system of the local device. When the program in the memory is executed by the processor, all or some of the functions in the above embodiments may be implemented.

The present disclosure has been described with reference to specific examples, which are merely for the purpose of facilitating understanding of the present disclosure and are not intended to limit the present disclosure. It will be apparent to those skilled in the art that changes may be made to the specific embodiments described above in accordance with the concept of the present disclosure.

What is claimed is:

1. A monitor, comprising:
  at least one physiological data monitoring module configured to monitor at least one physiological data of a patient, the at least one physiological data comprising at least one of ECG data, blood oxygen saturation data, body temperature data, respiratory data, heart rate data, or blood pressure data;
  a memory configured to store a program and the at least one physiological data;
  a touch display screen configured to receive a first touch screen operation under control of a processor; and
  the processor configured to run the program in the memory to implement the following processes:
    acquiring a first partition configuration of a display interface of the touch display screen, the first partition configuration comprising a first physiological data display area and a first function information display area;
    displaying the at least one physiological data in the first physiological data display area;
    displaying first function information different from the at least one physiological data in the first function information display area;
    detecting the first touch screen operation received by the touch display screen; and
    in response to determining that the first touch screen operation meets a preset re-partitioning rule:
      acquiring a second partition configuration of the display interface;
      switching a display of the display interface from the first partition configuration to the second partition configuration, the second partition configuration comprising a second physiological data display area and a second function information display area;
      partially or fully displaying the at least one physiological data in the second physiological data display area;
      displaying second function information different from the at least one physiological data in the second function information display area, the second function information comprising at least one of device information, device configuration information, or a device configuration button configured for user adjustment of device configuration attributes,
      wherein:
        an area of the second physiological data display area is smaller than that of the first physiological data display area, and an area of the second function information display area is greater than that of the first function information display area.

2. The monitor of claim 1, wherein:
  the area of the first physiological data display area is greater than that of the first function information display area; and
  the area of the second physiological data display area is smaller than that of the second function information display area.

3. The monitor of claim 1, wherein a distribution of the display interface obtained based on the second partition configuration uses at least one of the following methods:
  the second function information display area comprises a pop-up window, and the second physiological data display area partially or fully displays textual/numerical information of at least one physiological parameter corresponding to the at least one physiological data, but does not display waveform data; or
  the second physiological data display area partially or fully displays textual/numerical information or waveform data of at least one physiological parameter corresponding to the at least one physiological data.

4. The monitor of claim 1, wherein the processor is also configured to run the program in the memory to implement the following processes:
  switching the display of the display interface from the second partition configuration to the first partition configuration in response to any one of the following conditions being satisfied:
    no other touch screen operation is detected within a first preset duration;
    a second touch screen operation is detected in a preset region of the display interface; and
    a third touch screen operation that meets a first preset operation trajectory is detected.

5. The monitor of claim 4, wherein the first touch screen operation, the second touch screen operation, or the third touch screen operation comprises at least one of a single-finger sliding operation, a multi-finger sliding operation, or a tapping operation.

6. The monitor of claim 1, further comprising an external expansion screen, wherein the external expansion screen is coupled to the processor and is configured to simultaneously display a content that is displayed in the display interface.

7. The monitor of claim 1, wherein the second function information further comprises one or more of function configurations, function attributes, function buttons, patient information, alarm information, power information, volume information, attribute configuration buttons, or wireless information.

8. The monitor of claim 1, wherein:
  the second partition configuration further comprises a third function information display area; and
  the processor is further configured to run the program in the memory to:
  display at least one function button icon in the third function information display area, the at least one function button icon being configured to characterize a corresponding function operation.

9. The monitor of claim 8, wherein the third function information display area is located at an edge of the display of the display interface.

10. The monitor of claim 8, wherein the processor is also configured to run the program in the memory to implement the following processes:
  displaying a first part of the at least one function button icon in the third function information display area; and
  in response to detecting a fourth touch screen operation that meets a second preset operation trajectory in the third function information display area, displaying a second part of the at least one function button icon in the third function information display area.

11. The monitor of claim 8, wherein the processor is also configured to run the program in the memory to implement the following processes:
   displaying a first part of the at least one function button icon in the third function information display area; and
   in response to detecting a fifth touch screen operation for characterizing a movement of a target function button icon in the third function information display area, moving the target function button icon to a target position and rearranging the at least one function button icon in the third function information display area.

12. The monitor of claim 8, wherein the processor is also configured to run the program in the memory to implement the following processes:
   upon switching the display of the display interface to the second partition configuration, acquiring a third partition configuration of the display interface in response to detecting a sixth touch screen operation for characterizing hiding of the at least one function button icon, the third partition configuration comprising a third physiological data display area and a fourth function information display area;
   partially or fully displaying a content that was displayed in the second physiological data display area in the third physiological data display area; and
   displaying a content that was displayed in the second function information display area in the fourth function information display area.

13. A monitor, comprising:
   at least one physiological data monitoring module configured to monitor at least one physiological data of a patient, the at least one physiological data comprising at least one of ECG data, blood oxygen saturation data, body temperature data, respiratory data, heart rate data, or blood pressure data;
   a memory configured to store a program and the at least one physiological data;
   a touch display screen under control of a processor; and
   the processor configured to run the program in the memory to implement the following processes:
      acquiring a first partition configuration of a display interface of the touch display screen, the first partition configuration comprising a first physiological data display area and a first function information display area;
      displaying the at least one physiological data in the first physiological data display area;
      displaying first function information different from the at least one physiological data in the first function information display area;
      detecting an alarm event; and
      in response to the alarm event:
         acquiring a second partition configuration of the display interface, the second partition configuration comprising a second physiological data display area and a second function information display area;
         switching a display of the display interface from the first partition configuration to the second partition configuration;
         partially or fully displaying the at least one physiological data in the second physiological data display area;
         displaying second function information different from the at least one physiological data in the second function information display area, the second function information comprising at least one of device information, device configuration information, or a device configuration button configured for user adjustment of device configuration attributes,
   wherein:
      an area of the second physiological data display area is smaller than that of the first physiological data display area, and an area of the second function information display area is greater than that of the first function information display area.

14. The monitor of claim 13, wherein the processor is also configured to run the program in the memory to implement the following processes:
   switching the display of the display interface from the second partition configuration to the first partition configuration in response to determining that a duration of the alarm event exceeds a first preset duration, and no touch screen operation is detected within the duration.

15. A display method applied to a monitor, the display method comprising:
   acquiring a first partition configuration of a display interface of a touch display screen of the monitor, the first partition configuration comprising a first physiological data display area and a first function information display area;
   displaying at least one physiological data in the first physiological data display area;
   displaying first function information different from the at least one physiological data in the first function information display area;
   detecting a first touch screen operation received by the touch display screen;
   in response to determining that the first touch screen operation that meets a preset re-partitioning rule:
      acquiring a second partition configuration of the display interface;
      switching a display of the display interface from the first partition configuration to the second partition configuration, the second partition configuration comprising a second physiological data display area and a second function information display area;
      partially or fully displaying the at least one physiological data in the second physiological data display area;
      displaying second function information different from the at least one physiological data in the second function information display area, the second function information comprising at least one of device information, device configuration information, or a device configuration button configured for user adjustment of device configuration attributes,
   wherein:
      an area of the second physiological data display area is smaller than that of the first physiological data display area, and an area of the second function information display area is greater than that of the first function information display area.

16. The method of claim 15, further comprising:
   switching the display of the display interface from the second partition configuration to the first partition configuration in response to any one of the following conditions being satisfied:
      no other touch screen operation is detected within a second-preset duration; and
      a second touch screen operation is detected in a preset region of the display interface; and a third touch screen operation that meets a first preset operation trajectory is detected.

17. The method of claim 15, wherein the second function information further comprises one or more of function configurations, function attributes, function buttons, patient information, alarm information, power information, volume information, attribute configuration buttons, or wireless information.

18. A non-transitory storage medium, comprising a stored program, when executed by a device where the non-transitory storage medium is located, performs the display method applied to a monitor of claim 14.

19. The method of claim 15, wherein:
the second partition configuration further comprises a third function information display area; and
the method further comprises:
displaying at least one function button icon in the third function information display area, the at least one function button icon being configured to characterize a corresponding function operation.

20. The method of claim 19, further comprising:
upon acquiring the display of the display interface based on the first partition configuration, in response to an alarm event:
acquiring the second partition configuration of the display interface;
switching the display of the display interface from the first partition configuration to the second partition configuration;
partially or fully displaying the at least one physiological data in the second physiological data display area;
displaying the second function information different from the at least one physiological data in the second function information display area; and
displaying the at least one function button icon in the third function information display area.

21. The method of claim 20, further comprising:
switching the display of the display interface from the second partition configuration to the first partition configuration in response to detecting that a duration of the alarm event exceeding a first preset duration and no other touch screen operation within the first preset duration.

22. The method of claim 19, further comprising:
displaying a first part of the at least one function button icon in the third function information display area; and
in response to detecting a fourth touch screen operation that meets a second preset operation trajectory in the third function information display area, displaying a second part of the at least one function button icon in the third function information display area.

23. The method of claim 19, further comprising:
displaying a first part of the at least one function button icon in the third function information display area; and
in response to detecting a fifth touch screen operation for characterizing a movement of a target function button icon in the third function information display area, moving the target function button icon to a target position, and rearranging the at least one function button icon in the third function information display area.

24. The method of claim 19, further comprising:
upon acquiring the display of the display interface based on the second partition configuration, in response to a sixth touch screen operation for characterizing hiding of the at least one function button icon, acquiring a third partition configuration of the display interface, the third partition configuration comprising a third physiological data display area and a fourth function information display area;
partially or fully displaying a content that was displayed in the second physiological data display area in the third physiological data display area; and
displaying a content that was displayed in the second function information display area in the fourth function information display area.

* * * * *